United States Patent
Johnson et al.

(10) Patent No.: US 11,191,584 B2
(45) Date of Patent: Dec. 7, 2021

(54) DEAD-TIME OPTIMIZATION OF RESONANT INVERTERS BASED ON AN INPUT VOLTAGE OF A TANK

(71) Applicant: COVIDIEN LP, Mansfield, MA (US)

(72) Inventors: Joshua H. Johnson, Arvada, CO (US); James A. Gilbert, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 610 days.

(21) Appl. No.: 15/358,441

(22) Filed: Nov. 22, 2016

(65) Prior Publication Data

US 2017/0071655 A1 Mar. 16, 2017

Related U.S. Application Data

(63) Continuation of application No. 14/174,551, filed on Feb. 6, 2014, now Pat. No. 9,559,594.

(Continued)

(51) Int. Cl.
*H02M 3/335* (2006.01)
*A61B 18/12* (2006.01)
(Continued)

(52) U.S. Cl.
CPC ..... *A61B 18/1206* (2013.01); *H02M 3/33507* (2013.01); *H02M 7/537* (2013.01); *A61B 2017/0019* (2013.01); *A61B 2018/00684* (2013.01); *A61B 2018/00761* (2013.01); *A61B 2018/1286* (2013.01); *H02M 3/335* (2013.01); *H02M 3/33523* (2013.01); *H02M 7/4815* (2021.05)

(58) Field of Classification Search
CPC ............. H02M 3/335; H02M 3/33507; H02M 3/33523
See application file for complete search history.

(56) References Cited

U.S. PATENT DOCUMENTS

| | | | |
|---|---|---|---|
| 4,573,122 A | 2/1986 | Inbar et al. | |
| 6,856,526 B2 * | 2/2005 | Elek | H02M 7/003 363/86 |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

European Search Report No. 14159839.1 dated Jul. 8, 2014.
(Continued)

*Primary Examiner* — Kyle J Moody
*Assistant Examiner* — Lakaisha Jackson
(74) *Attorney, Agent, or Firm* — Carter, DeLuca & Farrell LLP

(57) ABSTRACT

The present disclosure is directed to an electrosurgical generator including a resonant inverter having an H-bridge and a tank. A sensor array measures at least one property of the tank. A pulse width modulation (PWM) controller outputs a first PWM timing signal and a second PWM timing signal to the H-bridge. The PWM controller controls a dead-time between the first PWM timing signal and the second PWM timing signal based on the at least one property measured by the sensor array.

20 Claims, 5 Drawing Sheets

Related U.S. Application Data

(60) Provisional application No. 61/838,753, filed on Jun. 24, 2013.

(51) Int. Cl.
  *H02M 7/537*  (2006.01)
  *A61B 18/00*  (2006.01)
  *H02M 7/48*   (2007.01)
  *A61B 17/00*  (2006.01)

(56) References Cited

U.S. PATENT DOCUMENTS

| | | | |
|---|---|---|---|
| 6,939,347 B2 | 9/2005 | Thompson | |
| D574,323 S | 8/2008 | Waaler | |
| 8,685,015 B2 | 4/2014 | Gilbert | |
| 9,559,594 B2 | 1/2017 | Johnson et al. | |
| 2005/0281058 A1 | 12/2005 | Batarseh et al. | |
| 2006/0007713 A1 | 1/2006 | Brown | |
| 2006/0290295 A1 | 12/2006 | Yang et al. | |
| 2010/0020569 A1* | 1/2010 | Melanson | H01F 38/02 363/21.03 |
| 2011/0279060 A1 | 11/2011 | Wang | |
| 2011/0279069 A1* | 11/2011 | Murata | H02P 25/06 318/128 |
| 2012/0095461 A1 | 4/2012 | Herscher et al. | |
| 2012/0105039 A1* | 5/2012 | Brown | H02M 1/08 323/283 |
| 2013/0013023 A1 | 1/2013 | Rezai | |
| 2013/0015887 A1 | 1/2013 | Piselli et al. | |
| 2013/0103023 A1 | 4/2013 | Monson et al. | |
| 2013/0147278 A1* | 6/2013 | Arisawa | H02P 8/12 307/75 |
| 2014/0146574 A1* | 5/2014 | Worek | H02M 3/3376 363/17 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0556705 A1 | 8/1993 |
| EP | 608609 A2 | 8/1994 |
| EP | 0836868 A2 | 4/1998 |
| EP | 880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 2469699 A2 | 6/2012 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| JP | 2004140913 A | 5/2004 |
| JP | 2005185657 A | 7/2005 |
| JP | 2012501696 A | 1/2012 |
| SU | 166452 | 1/1965 |
| SU | 727201 A2 | 4/1980 |
| WO | 9639086 A1 | 12/1996 |
| WO | 0211634 A1 | 2/2002 |
| WO | 0245589 A2 | 6/2002 |
| WO | 03090635 A1 | 11/2003 |
| WO | 2006050888 A1 | 5/2006 |
| WO | 2008053532 A1 | 5/2008 |
| WO | 2013017450 A2 | 2/2013 |

OTHER PUBLICATIONS

Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. Mi, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.

(56) References Cited

OTHER PUBLICATIONS

Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.

"Electrosurgical Unit Analyzer ESU-2400 Series User Manual" Apr. 1, 2002; Retrieved from Internet: <URL:http://www.bcgroupintl.com/ESU.sub.--2400/Updates/ESU-2400.sub.—UM.sub.—Rev04.pdf>, pp. 6, 11, 73.
U.S. Appl. No. 10/406,690, filed Apr. 3, 2003 inventor: Behnke.
U.S. Appl. No. 10/573,713, filed Mar. 28, 2006 inventor: Wham.
U.S. Appl. No. 10/761,524, filed Jan. 21, 2004 inventor: Wham.
U.S. Appl. No. 11/242,458, filed Oct. 3, 2005 inventor: Becker.
U.S. Appl. No. 14/096,341, filed Dec. 4, 2013 inventor: Johnson.
U.S. Appl. No. 14/098,859, filed Dec. 6, 2013 inventor: Johnson.
U.S. Appl. No. 14/100,113, filed Dec. 9, 2013 inventor: Gilbert.
U.S. Appl. No. 14/147,294, filed Jan. 3, 2014 inventor: Gilbert.
U.S. Appl. No. 14/147,312, filed Jan. 3, 2014 inventor: Gilbert.
U.S. Appl. No. 14/179,724, filed Feb. 13, 2014 inventor: Johnson.
U.S. Appl. No. 14/190,830, filed Feb. 26, 2014 inventor: Johnson.
U.S. Appl. No. 14/190,895, filed Feb. 26, 2014 inventor: Gilbert.
Mehrdad Jafarboland: "Analysis of an LCLC Resonant Converter with a Capacitive Output Filter" Journal of Power Electronics, vol. 11, No. 5, Sep. 20, 2011, pp. 662-6668.
European Search Report corresponding to European Application No. EP 14 16 8835, dated Dec. 15, 2014, 8 pages.
Chinese Office Action for application No. 201410254197.1 dated Sep. 4, 2017 with English Translation (15 pages).
Japanese Office Action for application No. 2014-117555 dated Feb. 28, 2018 with English translation (7 pages).
Australian Examination Report in corresponding Australian Application No. AU 2014202274 dated Apr. 28, 2018; 6 pages.
European Examination Report for Application No. 14168835.8 dated Jan. 11, 2019.
Australian Examination Report dated Feb. 15, 2019 for application No. 2018241133.
Canadian Office Action for Application No. 2850755 dated Jun. 5, 2020.

\* cited by examiner

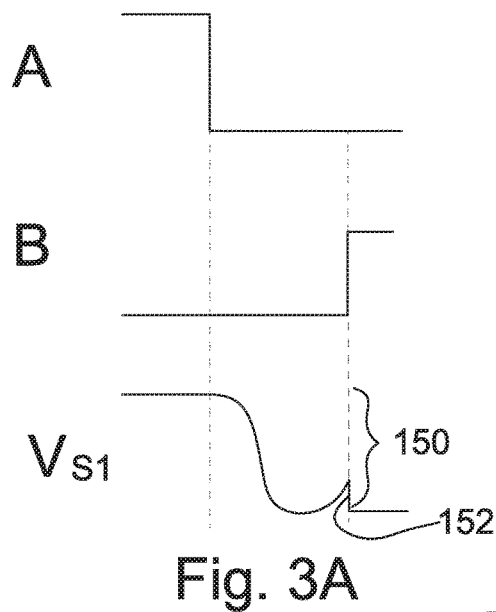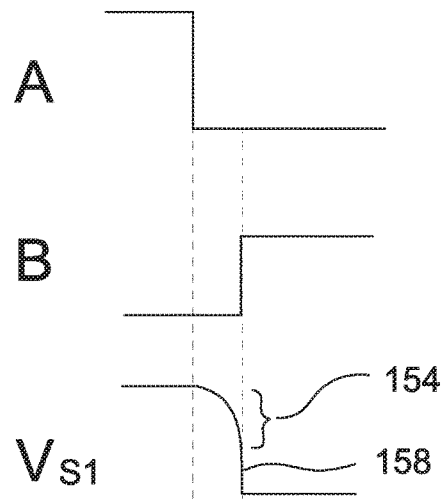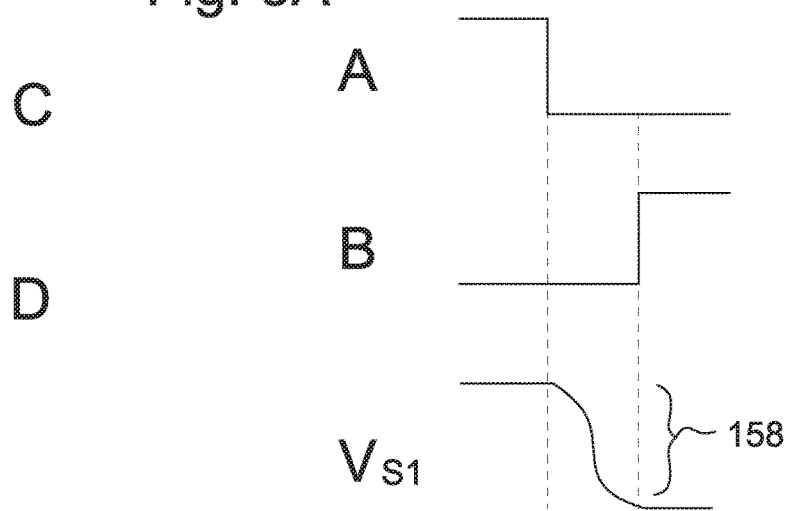

DEAD-TIME OPTIMIZATION OF RESONANT INVERTERS BASED ON AN INPUT VOLTAGE OF A TANK

CROSS REFERENCE TO RELATED APPLICATIONS

The present patent application is a continuation of U.S. patent application Ser. No. 14/174,551, filed Feb. 6, 2014, which claims the benefit of and priority to U.S. Provisional Patent Application Ser. No. 61/838,753, filed on Jun. 24, 2013. The entire contents of each of the foregoing applications are hereby incorporated herein by reference.

BACKGROUND

1. Technical Field

The present disclosure relates to radiofrequency amplifiers that use phase-shifted full bridge resonant inverters. Particularly, the present disclosure is directed to improving the efficiency and dynamic range of radiofrequency amplifiers.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. A source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated and the return electrode is placed remotely from the active electrode to carry the current back to the generator. In bipolar electrosurgery, one of the electrodes of the hand-held instrument functions as the active electrode and the other as the return electrode.

Electrosurgical generators may use a phase-shifted full bridge resonant inverter to generate the electrosurgical energy needed to perform the electrosurgical procedure. One example of a resonant inverter uses a LCLC tank topology driven by an H-bridge having two pairs of field effect transistors (FETs). Each pair of FETs includes two FETs that are connected in series. The two serially connected FETs should not be switched on at the same time or a short circuit would occur at the input voltage source. In order to avoid the short circuit, a fixed dead-time is provided between the pulse applied to the first FET and the pulse applied to the second FET among the pair of FETs. Depending on the load conditions of the resonant inverter, the optimal dead-times may also vary. If the dead-times of the FETs are too large or too short relative to the optimal dead-times, then the FET transition will be partially in zero-voltage switching and partially hard-switching. As the FETs hard-switch to a greater extent, the efficiency of the resonant inverter drops dramatically.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the term "generator" may refer to a device capable of providing energy. Such device may include a power source and an electrical circuit capable of modifying the energy outputted by the power source to output energy having a desired intensity, frequency, and/or waveform.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In an aspect of the present disclosure, an electrosurgical generator is provided. The electrosurgical generator includes a resonant inverter having an H-bridge and a tank. The generator also includes a sensor array configured to measure at least one property of the tank. A pulse width modulation (PWM) controller is provided and configured to output a first PWM timing signal and a second PWM timing signal to the H-bridge. The PWM controller controls a dead-time between the first PWM timing signal and the second PWM timing signal based on the at least one property measured by the sensor array.

In some aspects, the sensor array measures an input voltage, an output voltage and an output current and the PWM controller uses the input voltage, the output voltage, and the output current to determine the dead-time. The PWM controller calculates an efficiency measurement based on the input voltage and the output voltage. The PWM controller also calculates a load measurement based on the output voltage and the output current. The PWM controller controls the dead-time based on the efficiency measurement.

In some aspects, the PWM controller includes a memory having a look-up table stored thereon. The PWM controller determines a phase-shift of the H-bridge and a load measurement based the output voltage and the output current measured by the sensor array. The PWM controller determines the dead-time by comparing the phase-shift and the load measurement to data in the look-up table.

In another aspect of the present disclosure, a method for optimizing a dead-time for a field effect transistor (FET) transition in a resonant inverter is provided. The method includes initializing a dead-time for the FET transition and determining a first efficiency measurement of the resonant inverter. The dead-time of the FET transition is increased and a second efficiency measurement of the resonant inverter is determined. The dead-time is adjusted based on a comparison between the first efficiency measurement and the second efficiency measurement.

In some aspects, if the second efficiency measurement is greater than the first efficiency measurement by a predetermined percentage, the dead time is increased. If the second efficiency measurement is less than the first efficiency measurement by a predetermined percentage, the dead time is decreased.

In yet another aspect of the present disclosure, a method for optimizing a dead-time for a field effect transistor (FET) transition in a resonant inverter including an H-bridge and a tank is provided. The method includes determining a phase shift between a plurality of pulse width modulated signals applied to the H-bridge and determining a load measurement of the tank. The phase shift and the load measurement are compared to a look-up table and an optimal dead-time is determined based on a result of the comparison between the phase shift and the load measurement to the look-up table. The dead-time for the FET transition is adjusted based on the optimal dead-time.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3A is a graphical illustration of a voltage applied to an amplifier due to a large dead-time;

FIG. 3B is a graphical illustration of a voltage applied to an amplifier due to a short dead-time;

FIG. 3C is a graphical illustration of a voltage applied to an amplifier due to an optimized dead-time;

DETAILED DESCRIPTION

Figure 1:
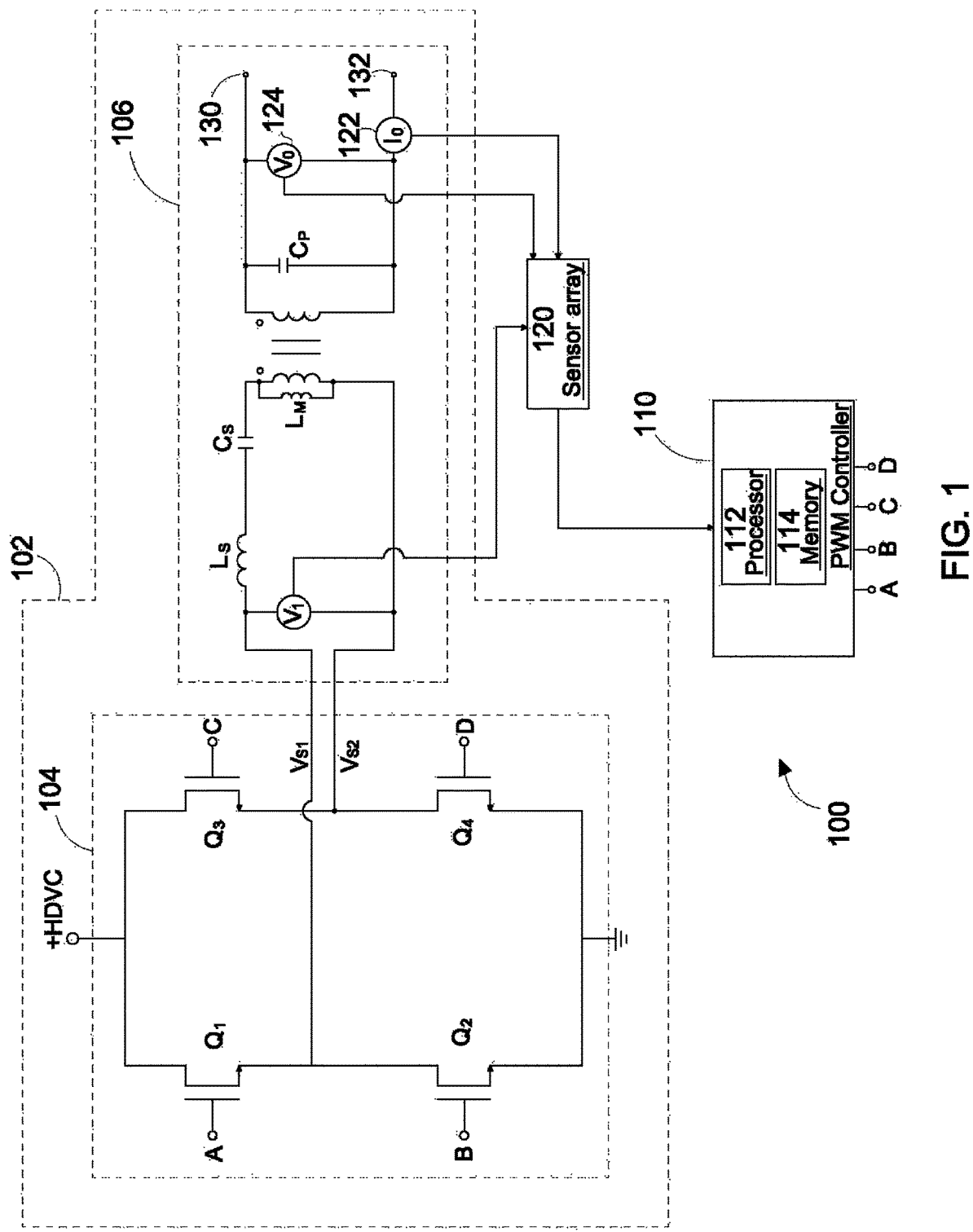
FIG. 1 is a schematic illustration of an electrosurgical generator in accordance with an embodiment of the present disclosure.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure is directed to an electrosurgical generator that employs a phase-shifted full bridge resonant inverter having an LCLC tank topology and an H-bridge. The generator utilizes a dead-time optimization algorithm to optimize the dead-time between pulses applied to the FETs in the H-bridge. By optimizing the dead-times, the efficiency and the dynamic range of the resonant inverter may be improved.

Turning to FIG. 1, one example of an electrosurgical generator in accordance with an embodiment of the present disclosure is shown generally as 100. The generator 100 includes suitable input controls (e.g., buttons, activators, switches, touch screen, etc.) for controlling the generator 100. In addition, the generator 100 may include one or more display screens (not shown) for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). An instrument (not shown) that may be connected to the generator 100 may also include a plurality of input controls that may be redundant with certain input controls of the generator 100. Placing the input controls at the instrument allows for easier and faster modification of RF energy parameters during the surgical procedure without requiring interaction with the generator 100.

The generator 100 may include a plurality of connectors to accommodate various types of electrosurgical instruments. Further, the generator 100 may operate in monopolar or bipolar modes by including a switching mechanism (e.g., relays) to switch the supply of RF energy between the connectors.

The generator 100 includes a resonant inverter circuit 102, a pulse width modulation (PWM) controller 110, and a sensor array 120. The resonant inverter circuit 102 includes an H-bridge 104 having FETs Q1, Q2, Q3, and Q4 and an LCLC tank 106. The PWM controller 110 includes a processor 112 and a memory 114.

Figure 2:
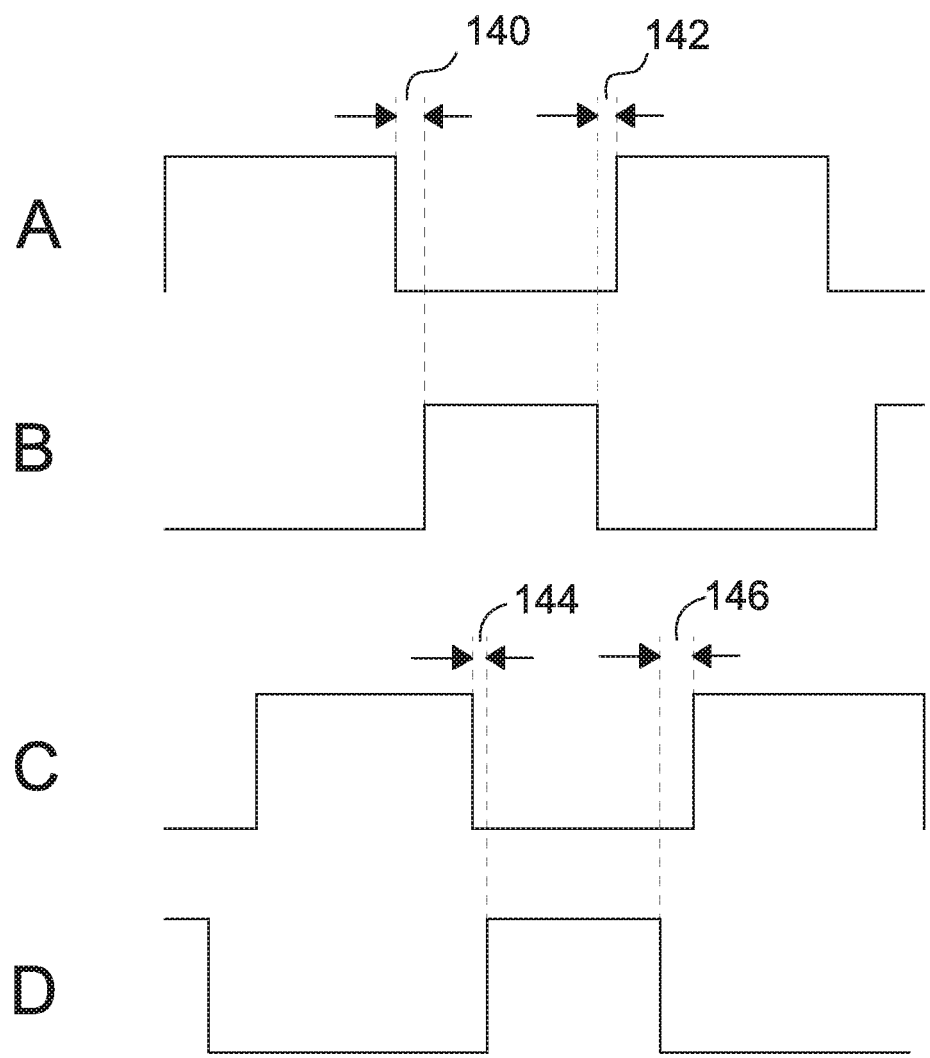
FIG. 2 is a timing diagram of the signal applied to the H-bridge shown in FIG. 1.

In the resonant inverter circuit 102, the H-bridge 104 is supplied with a positive high voltage direct current (+HVDC). The series-parallel, or LCLC, converters of LCLC tank 106 are driven in a full-bridge configuration by the active FET switches Q1, Q2, Q3 and Q4. The PWM controller 110 supplies phase-shifted PWM timing signals to FET switches Q1, Q2, Q3 and Q4 as shown in FIG. 2. FETs Q1 and Q2 provide a voltage $V_{S1}$ to the LCLC tank 106 and FETs Q3 and Q4 provide a voltage $V_{S2}$ to the LCLC tank 106.

Components $L_S$, $C_S$, $L_M$ and $C_P$ are selected to provide resonant output amplitudes that are proportional to the phase-shifted PWM duty cycles times the power supply rail +HVDC and ground. The LCLC tank 106 outputs electrosurgical energy to an instrument (not shown) via active terminal 130. In particular, the active terminal 130 provides either continuous or pulsed sinusoidal waveforms of high RF energy. The active terminal 130 is configured to provide a plurality of waveforms having various duty cycles, peak voltages, crest factors, and other suitable parameters. Certain types of waveforms are suitable for specific electrosurgical modes. For instance, the active terminal 130 may provide a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

A return terminal 132 is coupled to a return pad (not shown) for monopolar procedures. Alternatively, the return terminal 132 is electrically coupled to a return electrode (not shown) on an instrument.

The generator 100 may implement a closed and/or open loop control schemes which include the sensor array 120 having a plurality of sensors measuring a variety of tissue and energy properties (e.g., tissue impedance, tissue temperature, output current and/or voltage, etc.) and providing feedback to the PWM controller 110. A current sensor 122 can be disposed at either the active or return current path or both and provide an output current ($I_O$). A voltage sensor 124 can sense voltage at the terminals 130 and 132 and provide an output voltage ($V_O$). The output current and the output voltage are provided to the sensor array 120. Sensor array 120 may provide the output current and/or the output voltage to the PWM controller 110. The PWM controller 110 then transmits appropriate signals to FETs Q1, Q2, Q3, and Q4. The PWM controller 110 also receives input signals from the input controls of the generator 100 or the instrument. The PWM controller 110 utilizes the input signals to adjust power output by the generator 100 and/or performs other control functions thereon.

The sensor circuit 120 measures the input voltage ($V_I$) supplied to the LCLC tank 106, the output voltage ($V_O$) and output current ($I_O$) supplied by the active terminal 130 and the return terminal 132 in real time to characterize the electrosurgical process during a procedure. This allows for the measured electrical properties to be used as dynamic input control variables to achieve feedback control. The current and voltage values may also be used to derive other electrical parameters, such as power (P=V*I) and impedance (Z=V/I). The sensor circuit 120 may also measure properties of the current and voltage waveforms and determines the shape thereof.

The input voltage ($V_I$), the output voltage ($V_O$), and the output current ($I_O$) are provided to PWM controller 110 to implement a closed loop feedback scheme. As will be described in more detail below, the processor 112 of the PWM controller 110 implements an algorithm stored in memory 114 to adjust the dead-times of the PWM timing signals provided to FETs Q1, Q2, Q3, and Q4.

FIG. 2 depicts an example of the PWM timing signals A, B, C, and D that are provided to FETs Q1, Q2, Q3, and Q4, respectively. As shown in FIG. 2, the PWM signals A and B include a falling edge dead-time 140 and rising edge dead-time 142. The PWM signals C and D include a falling edge dead-time 144 and rising edge dead-time 146. Dead-time, as used in embodiments described herein, is the time interval between a change in a first input signal and a change in a second input signal. For instance, the dead-time 140 occurs between the falling edge of signal A and the rising edge of signal B. The dead-times 140, 142, 144, and 146 may be substantially similar or may vary depending on the algorithm that will be described hereinbelow.

FIGS. 3A-3C depict the voltage $V_{S1}$ applied to the LCLC tank 106 due to various dead-time situations. As shown in FIG. 3A, when the dead-time is larger than the optimal dead-time, the FET transition will be partially in zero voltage switching (150) and partially hard switching (152). As shown in FIG. 3B, when the dead-time is smaller than the optimal dead-time, the FET transition will be partially in zero voltage switching (154) and hard switching (156). Thus, when the dead-time is not optimal, the FET transition goes through a hard switching (152, 156) leading to a decrease in efficiency of the FETs. FIG. 3C depicts an optimal dead-time where the FET transition is in zero voltage switching (158) and there is no hard switching.

Figure 4:
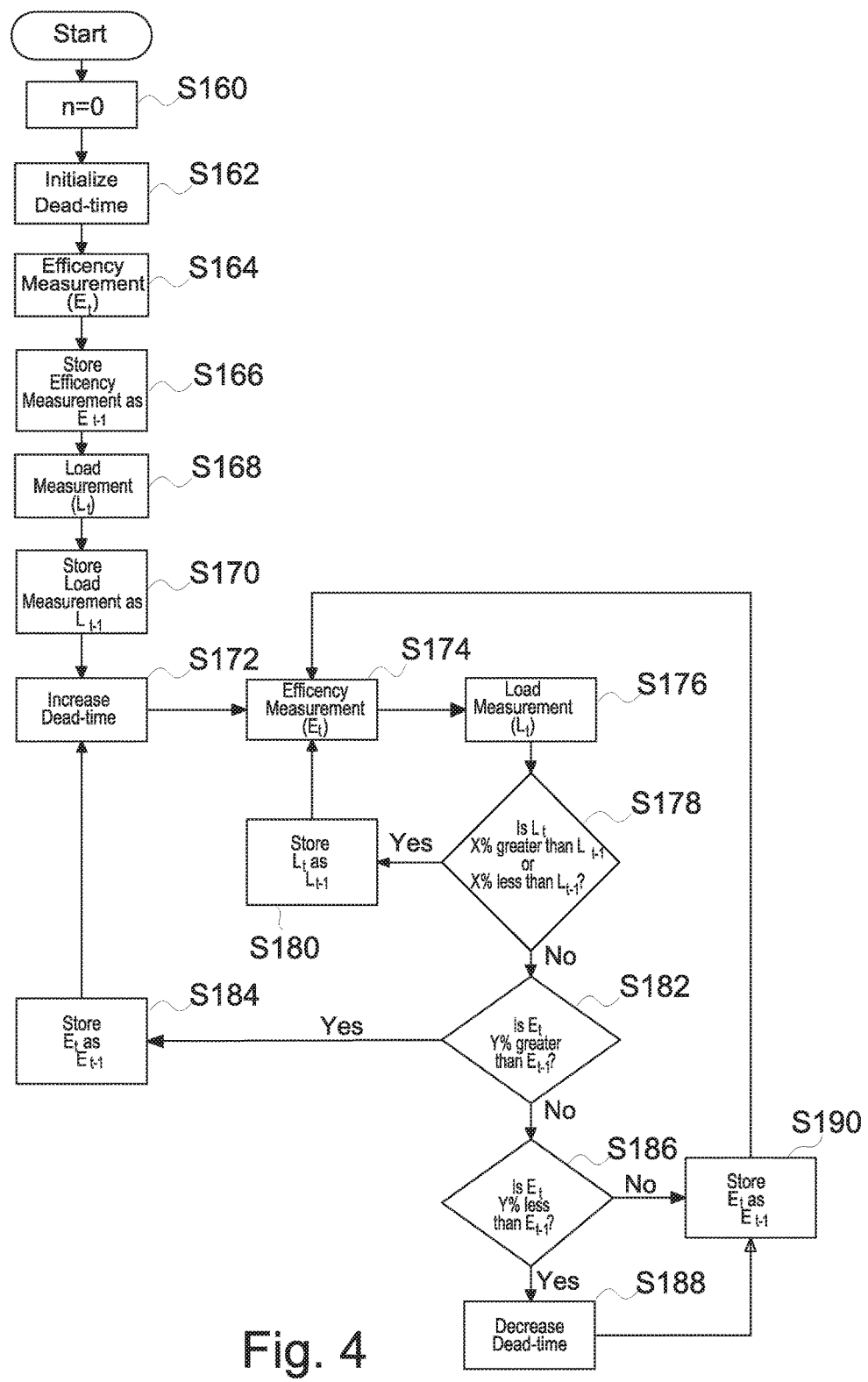
FIG. 4 is a flowchart depicting an optimization algorithm according to an embodiment of the present disclosure.

In an embodiment of the present disclosure, the dead-times of the PWM timing signals are optimized according to an algorithm as shown in the flowchart of FIG. 4. The algorithm shown in FIG. 4 is utilized to test the FET transition for each pair of FETs (i.e., a first pair including Q1 and Q2 and a second pair including Q3 and Q4). Turning to FIG. 4 in conjunction with FIG. 1, a counter is initialized to zero in step s160. The counter is implemented in the processor 112 or may be provided as a separate component in the PWM controller 110. The counter may be used to count the number of RF cycles, duration of time, etc. In step s162, an initial dead-time is selected for a FET transition. The dead-time may be a predetermined dead-time set by a manufacturer or it may be user set dead-time. The sensor circuit 120 measures the input voltage ($V_I$) and the output voltage ($V_O$) and processor 112 determines an efficiency measurement $E_t$ in step s164. The efficiency measurement $E_t$ is stored as $E_{t-1}$ in memory 114 in step s166. The sensor circuit 120 also measures the output current and processor 112 uses the output current and the output voltage measurement to determine the output impedance or load measurement $L_t$ in step s168. The load measurement $L_t$ is stored as $L_{t-1}$ in memory 114 in step s170.

After the efficiency measurement and the load measurement are stored as $E_{t-1}$ and $L_{t-1}$, the dead-time of the FET transition is increased in step s172. Another efficiency measurement $E_t$ and load measurement $L_t$ are taken in steps s174 and s176, respectively. In step s178, a comparison is made between $L_t$ and $L_{t-1}$. If $L_t$ is X % greater than or less than $L_{t-1}$, where X is a number programmed by a manufacturer or inputted by a user, then the algorithm proceeds to step s180 where the load measurement $L_t$ from step s176 is stored as $L_{t-1}$ and the algorithm returns to step s174. If $L_t$ is not X % greater than or less than $L_{t-1}$, then the algorithm proceeds to step s182 where a comparison is made between $E_t$ and $E_{t-1}$. If $E_t$ is Y % greater than $E_{t-1}$, where Y is a number programmed by a manufacturer or inputted by a user, then the algorithm proceeds to step s184 where the efficiency measurement $E_t$ from step s174 is stored as $E_{t-1}$ and the algorithm returns to step s172 to increase the dead time. If $E_t$ is not Y % greater than $E_{t-1}$, the algorithm proceeds to step s186 where a determination is made as to whether or not $E_t$ is Y % less than $E_{t-1}$. If $E_t$ is Y % less than $E_{t-1}$, then the algorithm proceeds the step s188 where the dead-time is decreased.

After the dead-time is decreased, the algorithm proceeds to step s190 where the efficiency measurement $E_t$ from step s174 is stored as $E_{t-1}$. If $E_t$ is not Y % less than $E_{t-1}$, then the algorithm skips the step s188 and goes to step s190. While the algorithm of FIG. 4 is used to optimize the dead-time of the FET transition, the counter continues to run until it reaches a predetermined value. When the counter at step s160 reaches the predetermined value. The algorithm is terminated and restarted for a different FET transition.

Figure 5:
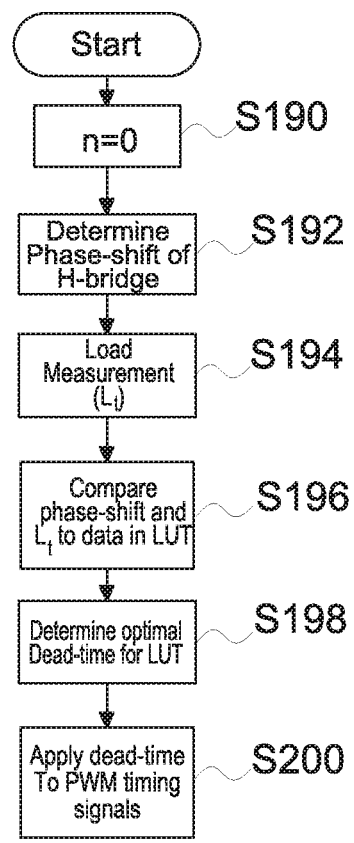
FIG. 5 is a flowchart depicting an optimization algorithm according to another embodiment of the present disclosure.

In another embodiment of the present disclosure, the dead-times of the PWM timing signals are optimized according to a look-up table (LUT) as shown in the flowchart of FIG. 5. The LUT is created by a manufacturer and stored in memory 118. Specifically, the optimal dead-times are empirically derived based on various phase-shifts of the H-bridge and load measurements. The optimal dead-times are then stored in the LUT with the corresponding phase-shift and load measurement data by the manufacturer. Turning to FIG. 5 in conjunction with FIG. 1, a counter is initialized to zero in step s190. The counter is implemented in the processor 112 or may be provided as a separate component in the PWM controller 110. The counter may be used to count the number of RF cycles, duration of time, etc. In step s192, a phase shift of the H-bridge is determined by processor 112. The phase shift is between the timing signals provided to the two pairs of FETs (Q1, Q2 and Q3, Q4) in the H-bridge 104, i.e., timing signals A-B and C-D. Each pair of FETs operates at a fixed duty cycle (e.g., 50%) minus the optimized dead time. The phase shift is proportional to the output power delivered to the load.

The sensor circuit 120 measures the output current ($I_O$) and the output voltage ($V_O$) to determine the output impedance or load measurement $L_t$ of the resonant inverter 102 in step s194. Processor 112 compares the phase shift of the H-bridge 104 and the load measurement $L_t$ to data in the LUT stored in memory 114 of the PWM controller 110. Based on the phase shift of the H-bridge 104 and the load measurement $L_t$, the processor 112 determines the optimal dead-time for the PWM timing signals in step s198. Specifically, the phase shifts of the H-bridge 104 and the load measurements of the resonant inverter 102 are compared to the phase shift and load measurement data in the LUT in step s196. The processor 112 then determines the optimal dead-time that corresponds to the phase shifts of the H-bridge and the load measurements of the resonant inverter 102 in step s198. The optimal dead times are applied to the PWM timing signals outputted by the PWM controller in step s200.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical generator comprising:
    a resonant inverter including an H-bridge and a tank, wherein the H-bridge includes a first field effect transistor (FET) and a second FET on a left side of the H-bridge, and a third FET and a fourth FET on a right side of the H-bridge, the first FET connected with the second FET at a first connection, and the third FET connected with the fourth FET at a second connection;
    a sensor array configured to measure at least an input voltage of the tank, wherein the input voltage is a voltage difference between a voltage at the first connection on the left side of the H-bridge and a voltage at the second connection on the right side of the H-bridge;
    a pulse width modulation (PWM) controller configured to output a first PWM timing signal and a second PWM timing signal to the H-bridge, wherein the PWM controller controls a dead-time between the first PWM timing signal and the second PWM timing signal based on the input voltage measured by the sensor array.

2. The electrosurgical generator of claim 1, wherein the sensor array measures an output voltage and an output current and the PWM controller uses the input voltage, the output voltage, and the output current to determine the dead-time.

3. The electrosurgical generator of claim 2, wherein the tank includes a transformer having a primary winding and a secondary winding, the output voltage being a voltage across the secondary winding.

4. The electrosurgical generator of claim 3, wherein the PWM controller controls the dead-time based on the input voltage and the output voltage.

5. The electrosurgical generator of claim 2, wherein the PWM controller calculates a load measurement based on the output voltage and the output current.

6. The electrosurgical generator of claim 2, wherein the PWM controller is further configured to:
    calculate a load measurement based on the output voltage and the output current; and
    determine whether the load measurement is less than a predetermined amount different from a previous load measurement, and
    wherein the output of the first PWM timing signal and the second PWM timing signal to the H-bridge is based on the determination.

7. The electrosurgical generator of claim 6, wherein the PWM controller is configured to output the first PWM timing signal and the second PWM timing signal when it is determined that the load measurement is less than the predetermined amount different from the previous load measurement.

8. The electrosurgical generator of claim 1, wherein the PWM controller includes a memory having a look-up table stored thereon.

9. The electrosurgical generator of claim 8, wherein the PWM controller determines a phase-shift of the H-bridge.

10. The electrosurgical generator of claim 9, wherein the sensor array measures an output voltage and an output current and the PWM controller determines a load measurement based the output voltage and the output current.

11. The electrosurgical generator of claim 10, wherein the PWM controller determines the dead-time by comparing the phase-shift and the load measurement to data in the look-up table.

12. A method for optimizing a dead-time for a field effect transistor (FET) transition in a resonant inverter having an H-bridge and a tank, the method comprising:
    initializing a dead-time for the FET transition;
    measuring a first input voltage of the tank, wherein the first input voltage is a first voltage difference between a first voltage at a first connection connecting a first FET and a second FET on a left side of the H-bridge, and a second voltage at a second connection connecting a third FET and a fourth FET on a right side of the H-bridge;

measuring a first output voltage of the tank;

increasing a dead-time of the FET transition;

measuring a second input voltage of the tank, wherein the second input voltage is a second voltage difference between a third voltage at the first connection and a fourth voltage at the second connection;

measuring a second output voltage of the tank; and adjusting the dead-time based on a comparison between at least the first input voltage of the tank and the first output voltage of the tank and the second input voltage of the tank and the second output voltage of the tank.

13. The method according to claim 12, wherein if the second input voltage of the tank and the second output voltage of the tank is greater than the first input voltage of the tank and the first output voltage of the tank by a predetermined percentage, the dead time is increased.

14. The method according to claim 12, wherein if the second input voltage of the tank and the second output voltage of the tank is less than the first input voltage of the tank and the first output voltage of the tank by a predetermined percentage, the dead time is decreased.

15. The method according to claim 12, wherein the tank comprises a transformer having a primary winding and a secondary winding and the first output voltage and the second output voltage are voltages across the secondary winding.

16. The method according to claim 12, further comprising:

measuring a first output current;

calculating a first load measurement based on the first output voltage and the first output current;

measuring a second output current;

calculating a second load measurement based on the second output voltage and the second output current; and determining whether the second load measurement is less than a predetermined amount different from the first load measurement, wherein the adjusting of the dead-time is further based on the determining.

17. The method according to claim 16, wherein the dead-time is adjusted when it is determined that the second load measurement is less than the predetermined amount different from the first load measurement.

18. A method for optimizing a dead-time for a field effect transistor (FET) transition in a resonant inverter including an H-bridge and a tank, the method comprising:

determining a phase shift between a plurality of pulse width modulated timing signals applied to the H-bridge;

determining a load measurement of the tank;

comparing the phase shift and the load measurement to a look-up table;

determining an optimal dead-time based on a result of the comparison between the phase shift and the load measurement to the look-up table; and adjusting the dead-time for the FET transition based on the optimal dead-time.

19. The method of claim 18, wherein the load measurement is determined based on an output current of the tank and an output voltage of the tank.

20. The method of claim 18, wherein the phase shift is proportional to an output power delivered to a load.

* * * * *